(12) United States Patent
Apacible et al.

(10) Patent No.: US 8,417,537 B2
(45) Date of Patent: Apr. 9, 2013

(54) EXTENSIBLE AND LOCALIZABLE HEALTH-RELATED DICTIONARY

(75) Inventors: Johnson T. Apacible, Mercer Island, WA (US); Sean Patrick Nolan, Bellevue, WA (US); Gaurav Dinesh Kalmady, Kirkland, WA (US); Vijay Varadan, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 535 days.

(21) Appl. No.: 11/860,627

(22) Filed: Sep. 25, 2007

(65) Prior Publication Data

US 2008/0103830 A1    May 1, 2008

Related U.S. Application Data

(60) Provisional application No. 60/863,897, filed on Nov. 1, 2006.

(51) Int. Cl.
*G06Q 10/00* (2012.01)
*G06Q 50/00* (2012.01)

(52) U.S. Cl.
USPC .................................. 705/2; 705/3; 707/999

(58) Field of Classification Search .................. 705/2–4; 707/999
See application file for complete search history.

(56) References Cited

U.S. PATENT DOCUMENTS

| | | |
|---|---|---|
| 5,213,555 A | 5/1993 | Hood et al. |
| 5,265,010 A | 11/1993 | Evans-Paganelli et al. |
| 5,690,582 A | 11/1997 | Ulrich et al. |
| 5,857,967 A | 1/1999 | Frid et al. |
| 5,890,995 A | 4/1999 | Bobick et al. |
| 5,924,074 A | 7/1999 | Evans |
| 6,002,982 A | 12/1999 | Fry |
| 6,013,007 A | 1/2000 | Root et al. |
| 6,057,758 A | 5/2000 | Dempsey et al. |
| 6,151,624 A | 11/2000 | Teare et al. |
| 6,253,208 B1 | 6/2001 | Wittgreffe et al. |
| 6,259,944 B1 | 7/2001 | Margulis et al. |
| 6,374,237 B1 | 4/2002 | Reese |

(Continued)

FOREIGN PATENT DOCUMENTS

| | | |
|---|---|---|
| JP | 2004-164052 A | 6/2004 |
| JP | 2005-165442 A | 6/2005 |

(Continued)

OTHER PUBLICATIONS

Peng Gong, et al. An Intelligent Middleware for Dynamic Integration of Heterogeneous Health Care Applications. http://ieeexplore.ieee.org/iel5/9520/30168/01385992.pdf?isNumber=. Last accessed on Aug. 1, 2007.

(Continued)

*Primary Examiner* — Michelle Le
(74) *Attorney, Agent, or Firm* — Hope Baldauff Hartman, LLC

(57) ABSTRACT

A system that uses a health-related dictionary component to establish responses to requests from devices and applications is provided. The innovation discloses uses of a health-related dictionary to enable retrieval of standardized lists and taxonomies in the healthcare space as well as localization of health-related data. Examples of these taxonomies include codes from medical coding vocabularies such as CPT (Current Procedural Terminology), layouts, templates, as well as references to units of measurements such as feet, inches, meters, liters, etc.

20 Claims, 10 Drawing Sheets

U.S. PATENT DOCUMENTS

| | | |
|---|---|---|
| 6,542,902 B2 | 4/2003 | Dulong et al. |
| 6,578,068 B1 | 6/2003 | Bowman-Amuah |
| 6,622,231 B2 | 9/2003 | Kaufman et al. |
| 6,692,435 B1 | 2/2004 | Choate |
| 6,704,798 B1 | 3/2004 | Mogul |
| 6,763,382 B1 | 7/2004 | Balakrishnan et al. |
| 6,912,534 B2 | 6/2005 | DeBettencourt et al. |
| 6,996,558 B2 | 2/2006 | Dettinger et al. |
| 7,082,427 B1 | 7/2006 | Selbel et al. |
| 7,111,172 B1 | 9/2006 | Duane et al. |
| 7,203,623 B2 | 4/2007 | Garcea et al. |
| 7,217,224 B2 | 5/2007 | Thomas |
| 7,230,529 B2 | 6/2007 | Ketcherside, Jr. et al. |
| 7,292,867 B2 | 11/2007 | Werner et al. |
| 7,317,927 B2 | 1/2008 | Staton et al. |
| 7,363,298 B2 | 4/2008 | Kadatch et al. |
| 7,398,263 B2 | 7/2008 | Dettinger et al. |
| 7,480,512 B2 | 1/2009 | Graham et al. |
| 7,603,255 B2 | 10/2009 | Case et al. |
| 7,613,722 B2 | 11/2009 | Horvitz et al. |
| 7,695,406 B2 | 4/2010 | Waters |
| 7,702,906 B1 | 4/2010 | Karr et al. |
| 7,730,528 B2 | 6/2010 | Chun et al. |
| 7,822,620 B2 | 10/2010 | Dixon et al. |
| 7,904,487 B2 | 3/2011 | Ghatare |
| 2001/0000358 A1 | 4/2001 | Isomichi et al. |
| 2001/0001147 A1 | 5/2001 | Hutchison et al. |
| 2001/0009454 A1 | 7/2001 | Manico et al. |
| 2002/0010679 A1 | 1/2002 | Flesher |
| 2002/0103811 A1 | 8/2002 | Fankhauser et al. |
| 2002/0120472 A1 | 8/2002 | Dvorak et al. |
| 2002/0126849 A1 | 9/2002 | Howard et al. |
| 2002/0129031 A1 | 9/2002 | Lau et al. |
| 2002/0138324 A1 | 9/2002 | Zarefoss et al. |
| 2002/0198739 A1 | 12/2002 | Lau et al. |
| 2003/0035371 A1 | 2/2003 | Reed et al. |
| 2003/0037054 A1 | 2/2003 | Dutta et al. |
| 2003/0037069 A1 | 2/2003 | Davidon |
| 2003/0051146 A1 | 3/2003 | Ebina et al. |
| 2003/0078934 A1* | 4/2003 | Cappellucci et al. ......... 707/101 |
| 2003/0081791 A1 | 5/2003 | Erikson et al. |
| 2003/0088438 A1 | 5/2003 | Maughan et al. |
| 2003/0149526 A1 | 8/2003 | Zhou et al. |
| 2003/0154406 A1 | 8/2003 | Honarvar et al. |
| 2003/0167274 A1 | 9/2003 | Dettinger et al. |
| 2003/0167456 A1 | 9/2003 | Sabharwal |
| 2003/0182361 A1 | 9/2003 | Jensen et al. |
| 2003/0212673 A1* | 11/2003 | Kadayam et al. ................. 707/3 |
| 2004/0017917 A1 | 1/2004 | Hammersmith et al. |
| 2004/0064502 A1 | 4/2004 | Yellepeddy et al. |
| 2004/0068653 A1 | 4/2004 | Fascenda |
| 2004/0088374 A1 | 5/2004 | Webb et al. |
| 2004/0088548 A1 | 5/2004 | Smetters et al. |
| 2004/0148276 A1 | 7/2004 | Dettinger et al. |
| 2004/0228492 A1 | 11/2004 | Park |
| 2005/0075996 A1 | 4/2005 | Dettinger et al. |
| 2005/0081039 A1 | 4/2005 | Lee et al. |
| 2005/0108537 A1 | 5/2005 | Puri et al. |
| 2005/0114501 A1 | 5/2005 | Raden et al. |
| 2005/0138417 A1 | 6/2005 | McNerney et al. |
| 2005/0144182 A1 | 6/2005 | Boris et al. |
| 2005/0165798 A1 | 7/2005 | Cherkauer et al. |
| 2005/0177749 A1 | 8/2005 | Ovadia |
| 2005/0197859 A1 | 9/2005 | Wilson et al. |
| 2005/0203771 A1 | 9/2005 | Achan |
| 2005/0210005 A1* | 9/2005 | Thompson et al. ............... 707/3 |
| 2005/0228808 A1 | 10/2005 | Mamou et al. |
| 2005/0239601 A1 | 10/2005 | Thomas |
| 2005/0251533 A1 | 11/2005 | Harken |
| 2005/0256834 A1 | 11/2005 | Millington et al. |
| 2005/0273365 A1 | 12/2005 | Baumgartner et al. |
| 2006/0004588 A1 | 1/2006 | Ananda |
| 2006/0005244 A1 | 1/2006 | Garbow et al. |
| 2006/0010127 A1 | 1/2006 | Dettinger et al. |
| 2006/0020506 A1 | 1/2006 | Axe et al. |
| 2006/0031094 A1 | 2/2006 | Cohen et al. |
| 2006/0089123 A1 | 4/2006 | Frank |
| 2006/0129540 A1 | 6/2006 | Hillis et al. |
| 2006/0150086 A1 | 7/2006 | Griffin et al. |
| 2006/0155584 A1 | 7/2006 | Aggarwal |
| 2006/0172724 A1 | 8/2006 | Linkert et al. |
| 2006/0178908 A1 | 8/2006 | Rappaport |
| 2006/0179003 A1 | 8/2006 | Steele et al. |
| 2006/0179178 A1 | 8/2006 | King |
| 2006/0206877 A1* | 9/2006 | Kohlmeier et al. ........... 717/137 |
| 2006/0229918 A1 | 10/2006 | Fotsch et al. |
| 2006/0277198 A1 | 12/2006 | Error et al. |
| 2006/0277215 A1 | 12/2006 | Siegel |
| 2007/0015532 A1 | 1/2007 | Deelman |
| 2007/0027961 A1 | 2/2007 | Holzer |
| 2007/0055552 A1 | 3/2007 | St. Clair et al. |
| 2007/0061318 A1 | 3/2007 | Azizi et al. |
| 2007/0073829 A1 | 3/2007 | Volodarsky et al. |
| 2007/0078686 A1 | 4/2007 | Dettinger et al. |
| 2007/0079332 A1 | 4/2007 | McEnroe et al. |
| 2007/0083393 A1 | 4/2007 | Howell |
| 2007/0118540 A1 | 5/2007 | Guo |
| 2007/0130044 A1 | 6/2007 | Rowan |
| 2007/0143273 A1* | 6/2007 | Knaus et al. ....................... 707/3 |
| 2007/0143342 A1 | 6/2007 | VanNostrand |
| 2007/0156655 A1 | 7/2007 | Butler et al. |
| 2007/0156842 A1 | 7/2007 | Vermeulen et al. |
| 2007/0157225 A1 | 7/2007 | Hrada et al. |
| 2007/0214015 A1 | 9/2007 | Christian |
| 2007/0220009 A1 | 9/2007 | Morris et al. |
| 2007/0237179 A1 | 10/2007 | Sethi |
| 2007/0239890 A1 | 10/2007 | Chen et al. |
| 2007/0266185 A1 | 11/2007 | Goddi et al. |
| 2007/0277228 A1 | 11/2007 | Curtis et al. |
| 2008/0033736 A1 | 2/2008 | Bulman |
| 2008/0101374 A1 | 5/2008 | West |
| 2008/0101597 A1 | 5/2008 | Nolan et al. |
| 2008/0103794 A1 | 5/2008 | Pettiross et al. |
| 2008/0103818 A1 | 5/2008 | Nolan et al. |
| 2008/0104012 A1 | 5/2008 | Nolan et al. |
| 2008/0104104 A1 | 5/2008 | Nolan et al. |
| 2008/0104615 A1 | 5/2008 | Nolan et al. |
| 2008/0104617 A1 | 5/2008 | Apacible et al. |
| 2008/0109158 A1 | 5/2008 | Huhtala et al. |
| 2008/0147790 A1 | 6/2008 | Malaney et al. |
| 2008/0172237 A1 | 7/2008 | Lai et al. |
| 2008/0306872 A1 | 12/2008 | Flesher |
| 2009/0013063 A1 | 1/2009 | Soman |
| 2009/0063665 A1 | 3/2009 | Bagepalli et al. |
| 2009/0064287 A1 | 3/2009 | Bagepalli et al. |
| 2009/0287837 A1 | 11/2009 | Flesher |
| 2010/0004097 A1 | 1/2010 | D'Eredita |
| 2010/0160014 A1 | 6/2010 | Galasso et al. |

FOREIGN PATENT DOCUMENTS

| | | |
|---|---|---|
| KR | 10-2004-0098962 A2 | 11/2004 |
| KR | 10-2006-0024560 | 3/2006 |
| KR | 10-2006-0024560 A1 | 3/2006 |
| WO | WO 2004/015542 | 2/2004 |
| WO | WO 2006/026673 A2 | 3/2006 |
| WO | 2008057973 | 5/2008 |

OTHER PUBLICATIONS

J. A. Maldonado, et al. A Mediator-Based Approach for the Integration of Distributed Electronic Healthcare Records. http://pangea.upv.es/weblogs/pedcremo/wp-content/articles/MEDICON2004.pdf. Last accessed on Aug. 1, 2007.

David J. Steiner, et al. Medical Data Abstractionism: Fitting an EMR to Radically Evolving Medical Information Systems. http://cmbi.bjmu.edu.cn/news/report/2004/medinfo2004/pdffiles/papers/4130Steiner.pdf. Last accessed on Aug. 1, 2007.

International Search Report for International Application No. PCT/US2007/083395, mailed Apr. 21, 2008, 4 pages.

Benefiting Healthcare Delivery with Secure Data Management. Http://www.sun.com/storagetek/docs/503238_5800_Healthcare_LF.pdf. Last accessed on Aug. 1, 2007.

Integrated Health Care Information System. Apr. 2004. http://www.ericsson.com/hr/products/e-health/Technical_Description_IHCIS_R2A.pdf.

Richard J. Gallagher, et al. An Audit Server for Monitoring Usage of Clinical Information Systems http://www.amia.org/pubs/symposia/D004856.pdf. Last accessed on Aug. 1, 2007.

Daniel R. Masys, et sl., Patient-Centered Access to Secure Systems Online (PCASSAO): A Secure Approach to Clinical Data Access via the World Wide Web. Http://medicine.ucsd.edu/pcasso/pubs/amia-oct97.pdf. Last accessed on Aug. 1, 2007.

OA dated Sep. 10, 2010 for U.S. Appl. No. 11/745,902, 21 pages.

OA dated Nov. 9, 2010 for U.S. Appl. No. 11/860,238, 19 pages.

OA dated Jan. 10, 2011 for U.S. Appl. No. 11/745,902, 21 pages.

Chinese OA, mailing date Dec. 27, 2010, for Chinese Application No. 200780040929.5, 7 pages.

Chinese OA, mailing date Dec. 27, 2010, for Chinese Application No. 200780040929.5, 9 pages.—Filed in IDS dated Feb. 4, 2011—refiling with full translation of CN OA.

OA dated Feb. 16, 2011 for U.S. Appl. No. 11/860,238, 22 pages.

International Search Report dated Mar. 16, 2009 in International Application No. PCT/US08/077552.

International Search Report dated May 22, 2009 in International Application No. PCT/US08/077563.

International Search Report dated Feb. 25, 2009 in International Application No. PCT/US08/077567.

Chinese Official Action dated Feb. 14, 2012 in Chinese Application No. 200780040929.5.

U.S. Official Action dated Apr. 11, 2012 in U.S. Appl. No. 11/745,902.

U.S. Official Action dated Aug. 5, 2010 in U.S. Appl. No. 11/745,904.

U.S. Official Action dated Jan. 24, 2011 in U.S. Appl. No. 11/745,904.

U.S. Official Action dated Aug. 8, 2011 in U.S. Appl. No. 11/745,904.

U.S. Notice of Allowance dated Feb. 17, 2012 in U.S. Appl. No. 11/745,904.

U.S. Official Action dated Aug. 5, 2010 in U.S. Appl. No. 11/745,898.

U.S. Official Action dated Dec. 23, 2010 in U.S. Appl. No. 11/745,898.

U.S. Official Action dated Mar. 17, 2011 in U.S. Appl. No. 11/745,898.

U.S. Official Action dated Aug. 18, 2011 in U.S. Appl. No. 11/745,898.

U.S. Official Action dated Dec. 8, 2011 in U.S. Appl. No. 11/745,898.

U.S. Official Action dated Mar. 30, 2012 in U.S. Appl. No. 11/745,898.

U.S. Official Action dated Sep. 18, 2009 in U.S. Appl. No. 11/759,359.

U.S. Official Action dated Apr. 14, 2010 in U.S. Appl. No. 11/759,359.

U.S. Official Action dated Aug. 4, 2010 in U.S. Appl. No. 11/759,359.

U.S. Official Action dated Jan. 20, 2011 in U.S. Appl. No. 11/759,359.

U.S. Official Action dated Nov. 10, 2011 in U.S. Appl. No. 11/759,359.

U.S. Official Action dated Jan. 6, 2011 in U.S. Appl. No. 11/759,361.

U.S. Official Action dated Jul. 8, 2011 in U.S. Appl. No. 11/759,361.

U.S. Official Action dated Apr. 1, 2010 in U.S. Appl. No. 11/760,218.

U.S. Official Action dated Aug. 13, 2010 in U.S. Appl. No. 11/760,218.

U.S. Official Action dated May 26, 2011 in U.S. Appl. No. 11/760,218.

U.S. Official Action dated Oct. 29, 2010 in U.S. Appl. No. 11/860,016.

U.S. Official Action dated May 13, 2011 in U.S. Appl. No. 11/860,016.

U.S. Official Action dated Nov. 17, 2009 in U.S. Appl. No. 11/860,371.

U.S. Official Action dated Apr. 23, 2010 in U.S. Appl. No. 11/860,371.

U.S. Official Action dated Nov. 19, 2010 in U.S. Appl. No. 11/860,371.

U.S. Official Action dated Mar. 9, 2011 in U.S. Appl. No. 11/860,371.

U.S. Official Action dated Jul. 15, 2011 in U.S. Appl. No. 11/860,371.

U.S. Official Action dated Nov. 17, 2011 in U.S. Appl. No. 11/860,371.

U.S. Official Action dated Jun. 14, 2010 in U.S. Appl. No. 11/860,381.

U.S. Official Action dated Mar. 4, 2011 in U.S. Appl. No. 11/860,381.

U.S. Official Action dated Oct. 21, 2011 in U.S. Appl. No. 11/860,381.

Holanda et al., "A Lossless Compression Method for Internet Packet Headers," 2005, Next Generation Internet Networks-IEEE, pp. 233-239.

Seals, The use of XML in Healthcare Information Management, Summer 2000, Journal of Healthcare Information Management, 14(2): 85-95.

"Design and Implementation Guidelines for Web Clients," 2003, Microsoft, retrieved Aug. 1, 2007 from http://www.willydev.net/descargas/PartnerAndPractices/WillyDev_DIGWC.pdf, 288 pages.

C. H. Crawford, et al. Toward an on Demand Service-Oriented Architecture. Aug. 2, 2007. https:/lwww.research.ibm.com/journal/sj/441/crawford.html, 24 pages.

Sriram Anand. "Managing Enterprise Data Complexity Using Web Services: Part 1," Jun. 28, 2005, retrieved from http://webservices.sys-con.com.read/104940__2.htm., 3 pages.

"Creating a Custom Data Paging Solution with IBM WebSphere Portlet Factory," Jun. 21, 2007. http://download.boulder.ibm.com/ibmdl/pub/software/dw/wes/pdf/wpfsamps/CustomDataPaging.pdf. 5 pages.

U.S. Official Action dated Jul. 19, 2012 in U.S. Appl. No. 11/759,359.

U.S. Official Action dated Jul. 19, 2012 in U.S. Appl. No. 11/860,016.

U.S. Notice of Allowance dated Jun. 19, 2012 in U.S. Appl. No. 11/745,904.

Mudigonda et al., "Overcoming the memory wall in packet processing: Hammers or Ladders," 2005, ANC S Symposium, pp. 1-10.

Tohru, Ishiguro, "Challenge to Grid System Using OGSA GT3; Service Oriented System by Grid," Mar. 1, 2004, Java Developer, No. 20, pp. 72-79, Softbank Publishing, Japan.

Japanese Official Action dated Jun. 8, 2012 in Japanese Application No. 2009-535477.

U.S. Official Action dated Oct. 11, 2012 in U.S. Appl. No. 11/745,902.

U.S. Official Action dated Oct. 25, 2012 in U.S. Appl. No. 11/860,381.

U.S. Official Action dated Jan. 9, 2013 in U.S. Appl. No. 11/759,359.

* cited by examiner

EXTENSIBLE AND LOCALIZABLE HEALTH-RELATED DICTIONARY

CROSS REFERENCE TO RELATED APPLICATIONS

This application claims the benefit of U.S. Provisional Patent Application Ser. No. 60/863,897 filed on Nov. 1, 2006, entitled "INTERACTIVE AND INTUITIVE HEALTH AND FITNESS TRACKING," and is related to U.S. patent application Ser. No. 11/745,898 filed on May 8, 2007, entitled "HEALTH INTEGRATION PLATFORM SCHEMA" the entireties of which are incorporated herein by reference.

BACKGROUND

The evolution of computers and networking technologies from high-cost, low performance data processing systems to low cost, high-performance communication, problem solving, and entertainment systems has provided a cost-effective and time saving means to lessen the burden of performing every day tasks such as correspondence, bill paying, shopping, budgeting information and gathering, etc. For example, a computing system interfaced to the Internet, by way of wire or wireless technology, can provide a user with a channel for nearly instantaneous access to a wealth of information from a repository of web sites and servers located around the world. Such a system, as well, allows a user to not only gather information, but also to provide information to disparate sources. As such, online data storing and management has become increasingly popular.

For example, collaborative social networking websites have exploded world-wide. These sites allow users to create remotely stored profiles including personal data such as age, gender, schools attended, graduating class, places of employment, etc. The sites subsequently allow other users to search the foregoing criteria in an attempt to locate other users—be it to find a companion with similar interests or locate a long lost friend from high school. As another more practical example, banking websites offer users the ability to remotely store information concerning bills to be paid. By utilizing this feature, users can automatically schedule bill payments to be made from their bank account which will be automatically debited when the payment is scheduled. This allows simultaneous electronic management of account balancing and bill paying so as to save the user from manually entering checks into the register of their checkbook.

Another area of great interest in this country and the entire world is personal health and fitness. Many vastly differing concerns can be discussed in this area, such as setting and obtaining personal fitness goals and the vastly disparate topic of the inefficiencies existing in our health system. For example, today an individual wishing to receive pharmaceutical treatment for illness must first see their primary care physician. Before seeing the physician, the patient will, many times, be required to show their health insurance coverage card. During the visit, the physician will typically write a prescription for the patient. The patient, then, takes the prescription to the pharmacy for fulfillment at which time they may need to furnish their health insurance coverage card again. The pharmacy fills the prescription, notifies insurance, deducts any coverage amount and transfers the prescription to the patient upon payment of the balance. These manual steps are time-consuming, annoying, inefficient, and prone to errors. As well, data associated with these steps is most often retained within distributed and disparate stores.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that uses a health-related dictionary component to establish responses to requests from applications. Effectively, the innovation discloses uses of a health-related dictionary to enable retrieval of standardized lists and taxonomies in the healthcare space. Examples of these taxonomies include codes from medical coding vocabularies such as CPT (Current Procedural Terminology), layouts, templates, as well as references to units of measurements such as feet, inches, meters, liters, etc.

In addition to providing simple definitions and other reference materials, the innovation discloses mechanisms to transform and/or localize information such that it conforms to local customs and practices. For example, information can be translated into a local language/dialect, formatted in accordance with local custom or the like. In these examples, a profile can be used to define local policies/preferences associated with a user and/or application.

In still other aspects, the dictionary component can communicate synchronously and/or asynchronously with a plurality of applications. For instance, an application can range from software applications to software application executed by way of electronic devices. Accordingly, most any device and/or application can generate a request to the dictionary component in accordance with the scope of the innovation.

In yet another aspect thereof, artificial intelligence and machine learning & reasoning logic components are provided that employ a probabilistic and/or statistical-based analysis to prognose or infer an action that a user desires to be automatically performed.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
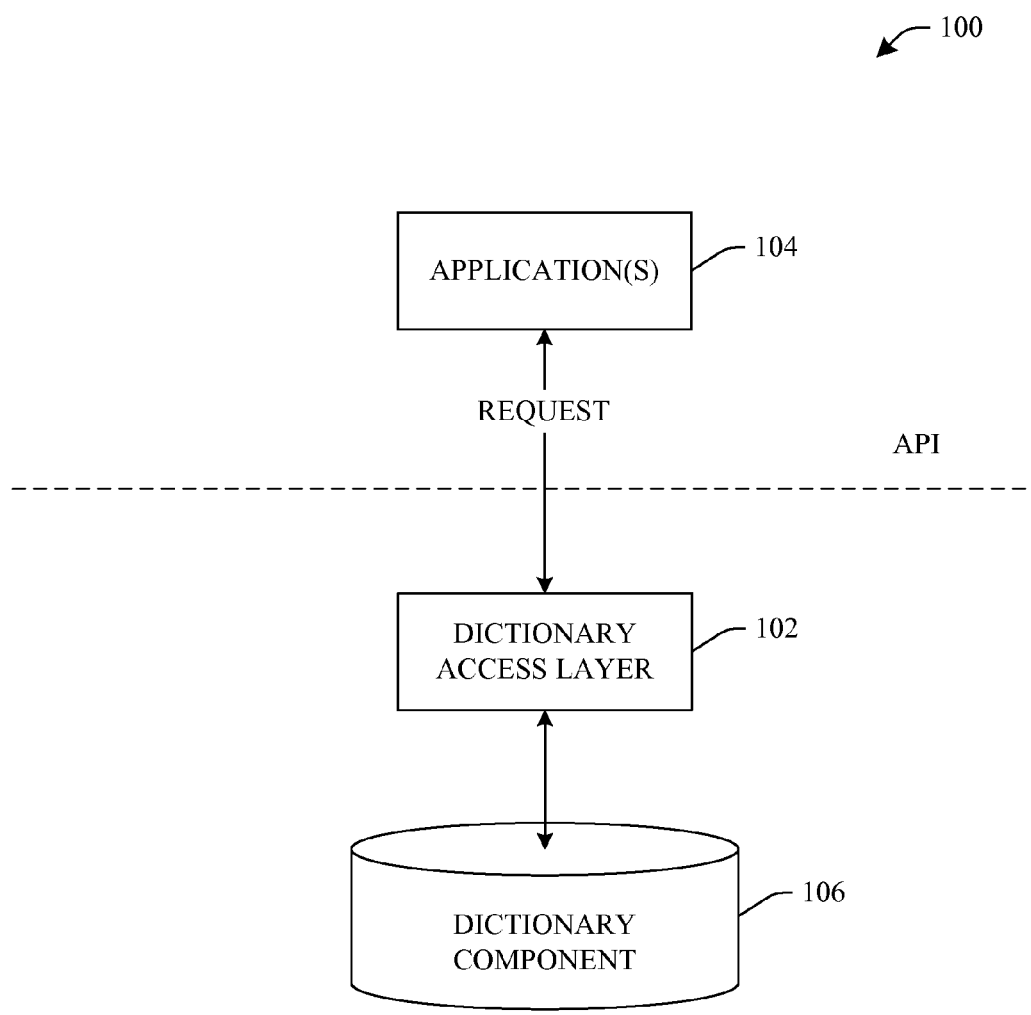
FIG. 1 illustrates a system that facilitates accessing a health-related dictionary in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that facilitates employment of a dictionary associated with a health-related network. In general, system 100 employs a dictionary access layer 102 that enables requests from applications 104 to communicate and/or retrieve information from dictionary component 106. Effectively, the dictionary access layer 102 enables applications to communicate with a health-related network as described in the Related Application set forth above and incorporated by reference herein. In managing requests, the dictionary access layer 102 provides an extensible and localizable health dictionary which can, among other things, define acronyms, procedures and vocabulary, transform units of weight, measurement, localize formats, etc.

In operation, the dictionary access layer 102 enables retrieval of standardized lists/taxonomies from this health-related information platform. In other words, applications 104 that are built on top of a health integration platform (as set forth in the Related Application incorporated by reference above) employ the dictionary access layer 102 as a facility to retrieve/access standardized lists/taxonomies within this platform. Examples of these lists/taxonomies include codes from medical coding vocabularies such as CPT (Current Procedural Terminology), ICD9CM (International Statistical Classification of Diseases and Related Health Problems, Ninth Revision, Clinical Modification), units of measurements like feet, inches, meters. Since these applications 104 are part of a unified ecosystem, it becomes imperative that these lists/taxonomies are handled in a common way in the health-related information platform for use across the application space. Accordingly, the dictionary access layer 102 provides mechanisms to store, localize, expand, and customize these lists/taxonomies.

Upon a review of the aforementioned Related Application, it will be understood that the dictionary component 106 can be used as a key part of the health integration platform by providing reference, transformation, and localization services. The dictionary component 106 uses a repository as storage in the back-end. It will be appreciated that the repository schema can support localization. As will be described in greater detail below, the dictionary component can have a middle tier that performs translations through XSLT (Extensible Stylesheet Language Transformation) that enables customization of localized results. Moreover, the dictionary component 106 can include a set of well-defined APIs (application program interfaces) that enables vocabularies to be queried.

Figure 2:
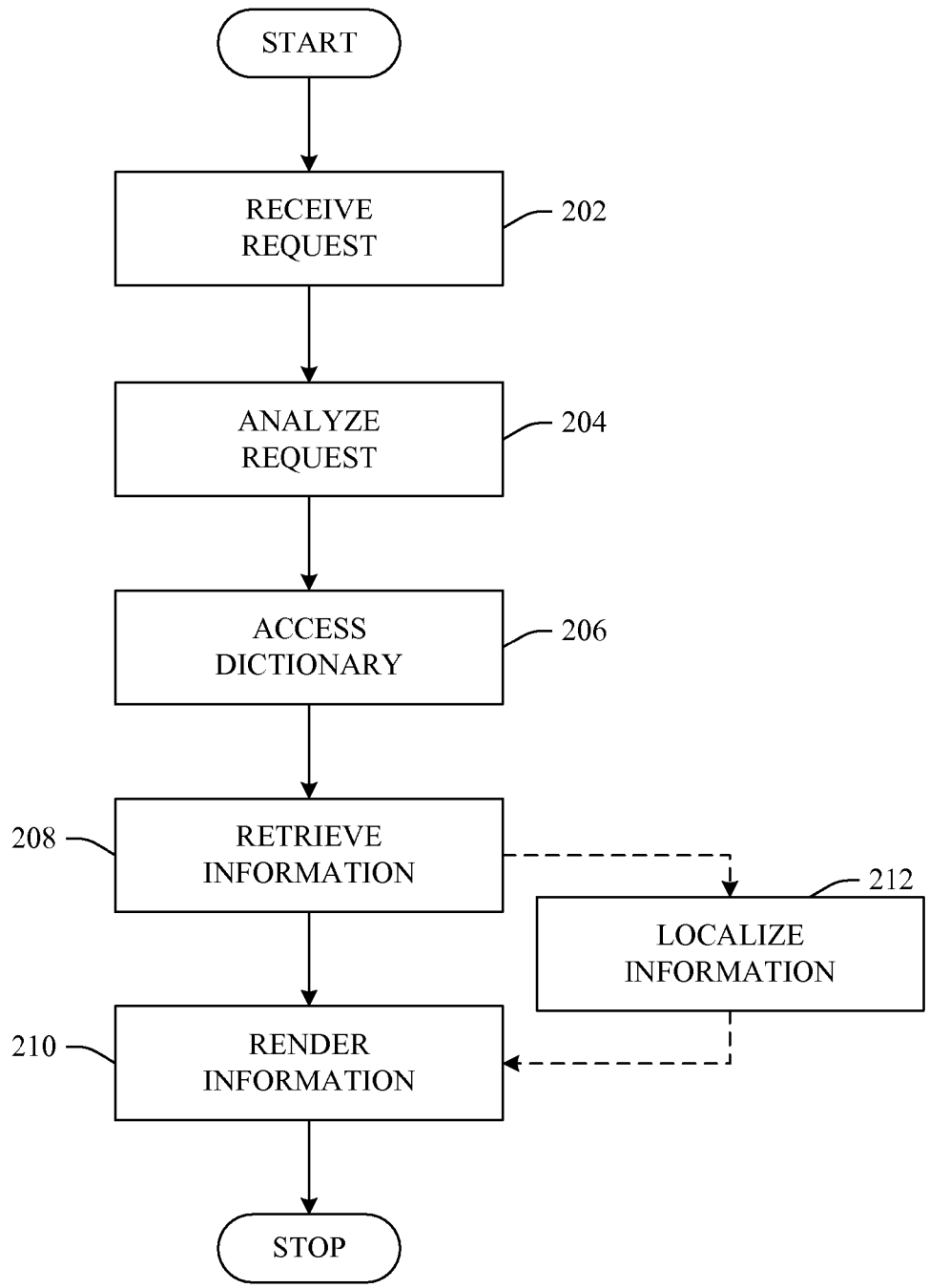
FIG. 2 illustrates an example flow chart of procedures that facilitate processing a dictionary request in accordance with an aspect of the innovation.

FIG. 2 illustrates an example methodology of establishing access to a dictionary component in accordance with an aspect of the innovation. The example methodology illustrated in FIG. 2 depicts an example flow of acts that facilitate accessing, transforming and localizing information from a health-related information dictionary. As will be described below, this information can range from acronyms, vocabulary, medical procedures, units of measurements, localization display characteristics, among others.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 202, a request can be received from an application, for example, a request to decipher an acronym that corresponds to a medical procedure. In another example, the request can be a request to transform a unit of measurement. In still other examples, the access to the dictionary can include a request to localize (e.g., format, configure) health-related information.

The request can be analyzed at 204 in order to determine information desired from the dictionary. The dictionary is accessed at 206 and information is received at 208. It is to be understood that the information received can be configured in a format acceptable for rendering. Else, appropriate formats, renderings or transforms can be applied to the retrieved information prior to rendering at 210.

In still other aspects, as optionally illustrated by dashed lines, at 212, the information can be localized to conform to a desired locale. For example, the information can be translated into a local language/dialect, formatted to conform to local custom, or the like. It is to be understood that most any configuration can be performed on the dictionary information prior to rendering to the requester (e.g., application, user). It is further to be understood and appreciated that rules (e.g., implementation schemes) can be applied in order to configure the information. These alternative aspects are to be included within the scope of the innovation and claims appended hereto.

As will be appreciated upon a reading of this disclosure and claims appended hereto, the innovation includes the architectures, the actual APIs and the schemas employed to establish and use the dictionary within the healthcare domain. These APIs are used to communicate with the platform to get health related taxonomies. The schema is used to store a variety of taxonomies within a health-related network, each of which conforms to a structure with different representational needs and also contains structures to help efficiently return localized versions of these taxonomies. The localization aspect of thing transforms can also draw its logic from the dictionary subsystem.

It will further be understood and appreciated that the control of the dictionary subsystem API and schema enables protection of investments and would facilitate an offering of a unique resource in the healthcare space in terms of the ability to store and retrieve health and wellness data in a predictable and extensible fashion.

The following discussion is provided to add context of the dictionary concepts within the healthcare space. As such, this discussion is not intended to limit the scope of the innovation in any manner. Rather, it will be understood that other features, functions and benefits exist in addition to those discussed in connection with FIG. 3 that follows.

Figure 3:
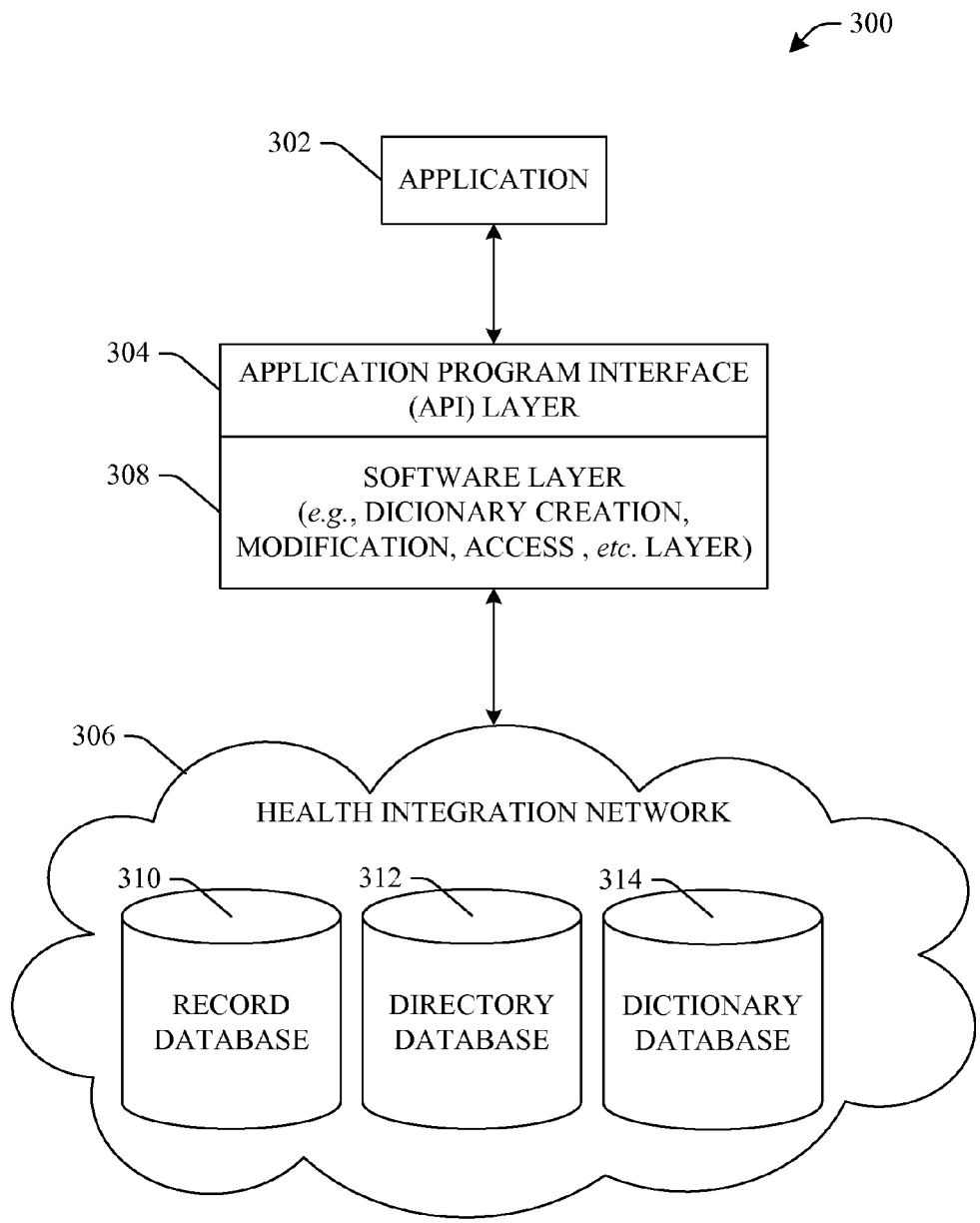
FIG. 3 illustrates an example system that provides an application access to a health integration network in accordance with an aspect of the innovation.

Referring now to FIG. 3, an example system 300 that facilitates accessing information within a health integration network according to a schema is shown. An application 302 can at least one of display or specify health related data. It is to be appreciated that the application 302 can be many different types of applications, including software applications, electronic devices executing a software application, electronic devices alone, legacy devices interfaceable with a device executing a software application, and the like. The application can utilize the API 304 to request and/or store data within a health integration network 306. It is to be appreciated that the API 304 can synchronously or asynchronously communicate with a plurality of applications 302 of similar or different types.

The API 304 can also include a software layer 308 (e.g., dictionary creation, modification, or access layer) that leverages in interpreting and processing a request or data from an application 302. The software layer 308 can be separated as shown, or it can be integrated within the API 304, the health integration network 306, or both. Upon interpreting and processing a request from the application 302, the API 304 can process the request, and/or can leverage the software layer 308 for access to dictionary information.

By way of another example, the software layer 308 can translate external vocabularies in order to make them compatible with the health integration network 306. As shown, the health integration network 306 can comprise a plurality of data stores including a record repository 310, a directory repository 312, and a dictionary repository 314. In addition, the health integration network 306 can comprise many other systems and/or layers to facilitate data management, transfer and access. Furthermore, the repositories can be redundant such that multiple versions of respective repositories are available for other APIs and applications and/or a back-up source for other versions of the repositories. Additionally, the repositories can be logically partitioned among various physical data stores to allow efficient storage and retrieval for highly accessed systems.

Providing separate partitions and/or repositories can allow varying levels of security across the disparate partitions/repositories. This can be advantageous to provide compliance with regulations, for example, such as Health Insurance Portability and Accountability Act (HIPAA) where perhaps the health records need tight security to be in compliance with HIPAA requirements, but data types and vocabulary lookups can require little or no security. Moreover, the repositories can be hierarchically based, such as XML (extensible markup language) and/or relationally based.

The record repository 310 can be highly distributed and comprise personal health related data records for a plurality of users. Thus, it can be beneficial for the record repository to be distributed to many different types of repositories even—relational and hierarchical (XML) alike. In this regard, the health integration network 306 can support a plurality of different architectures and structures. The records can be of different formats and can comprise most any kind of data (single instance, structured or unstructured), such as plain data, data and associated type information, self-describing data (by way of associated schemas, such as XSL schemas for example), data with associated templates (by way of stylesheets for example), data with units (such as data with conversion instructions), binary data (such as pictures, x-rays, etc.), and the like.

Moreover, the record repository 310 can keep an audit trail of changes made to the records for tracking and restoration purposes; a schema component (not shown) can automatically enter records into the audit trail portion of the record repository 310 upon modification of the records, authorization rules related to the records and the like. Additionally, any data type or related instances of the foregoing information can be stored in a disparate repository such as the dictionary repository 314 described infra. The record repository 310 can be partitioned, distributed, and/or segmented based on a number of factors including performance, logical grouping of users (e.g. users of the same company, family, and the like).

The directory repository 312 can store information such as user account data, which can include user name, authentication credentials, the existence of records for the user, etc. The directory repository 312 can also house information about records themselves including the user to whom they belong, where the record is held (in a distributed record repository 310 configuration) authorization rules for the records, etc. For example, a user can specify that a spouse have access to his/her fitness related data, but not medical health related data. In this way, a user can protect his/her data while allowing appropriate parties (such as spouse, doctor, insurance company, personal trainer, etc.) or applications/devices (blood pressure machine, pacemaker, fitness watch, etc.) to have access to relevant data. In addition, the directory repository 312 can comprise data regarding applications 312 that interact with the health integration network 306; applications 302 can be required to register with the health integration network 306, and thus, the application data in the directory repository 312 can include the registration information.

The dictionary repository 314 can hold information relating to vocabulary definitions used by the health integration network 306 and requesting entities such as the API 304 and software layer 308. Such definitions can include data type definitions and information on how to display the different data types or transform them. Additionally, the dictionary repository 314 can hold information for display layouts and templates, etc. Furthermore, the dictionary repository 314 can hold different look-up tables that define codes through the use of standards and the like. For example, the dictionary repository 314 can support International Classification of Diseases, ninth revision (ICD-9) released by the National Center for Health Statistics. These codes identify different diseases and diagnoses; thus a doctor can put one of these codes on a user's chart in the health integration network 314, and the dictionary repository 314 can allow the software layer 308 (or API 304) to translate this code into something that makes more sense to the user, such as medical name and/or different, other, or additional information concerning the diagnosis.

Separating the repositories and providing authentication/authorization information to be stored, for example, in the directory repository 312 allows application developers to utilize the health integration network 306 without having to implement authentication/authorization procedures for use with the applications 302. Moreover, the repositories can provide record level authorizations as an additional layer of security. The dictionary repository 314 can also be used to retrieve other metadata such as plural and abbreviated forms of the codes. It can also hold information that allows conversion between different measurement units, such as between feet to meters, Fahrenheit to Celsius, etc.

In one embodiment, the application 302, which can be more than one application 302, can make a call to the API 304 to convert data, for example. The API 304 can leverage the software layer 308 to process the call made by the application 304. The software layer 308 can then utilize the dictionary repository 314 to access definitions and in this particular example, to convert data into a particular desired unit(s). Still further, the dictionary component 314 can also be used to automatically configure or format the data into a format consistent with a desired locale.

The aforementioned systems, architectures and the like have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component to provide aggregate functionality. Communication between systems, components and/or sub-components can be accomplished in accordance with either a push and/or pull model. The components may also interact with one or more other components not specifically described herein for the sake of brevity, but known by those of skill in the art.

Furthermore, as will be appreciated, various portions of the disclosed systems and methods may include or consist of artificial intelligence (AI), machine learning & reasoning (MLR), or knowledge or rule based components, sub-components, processes, means, methodologies, or mechanisms (e.g., support vector machines, neural networks, expert systems, Bayesian belief networks, fuzzy logic, data fusion engines, classifiers . . . ). Such components, inter alia, can automate certain mechanisms or processes performed thereby to make portions of the systems and methods more adaptive as well as efficient and intelligent, for instance by inferring actions based on contextual information. By way of example and not limitation, such mechanisms can be employed with respect to generation of data definition, conversion, transformation, localization and the like.

Figure 4:
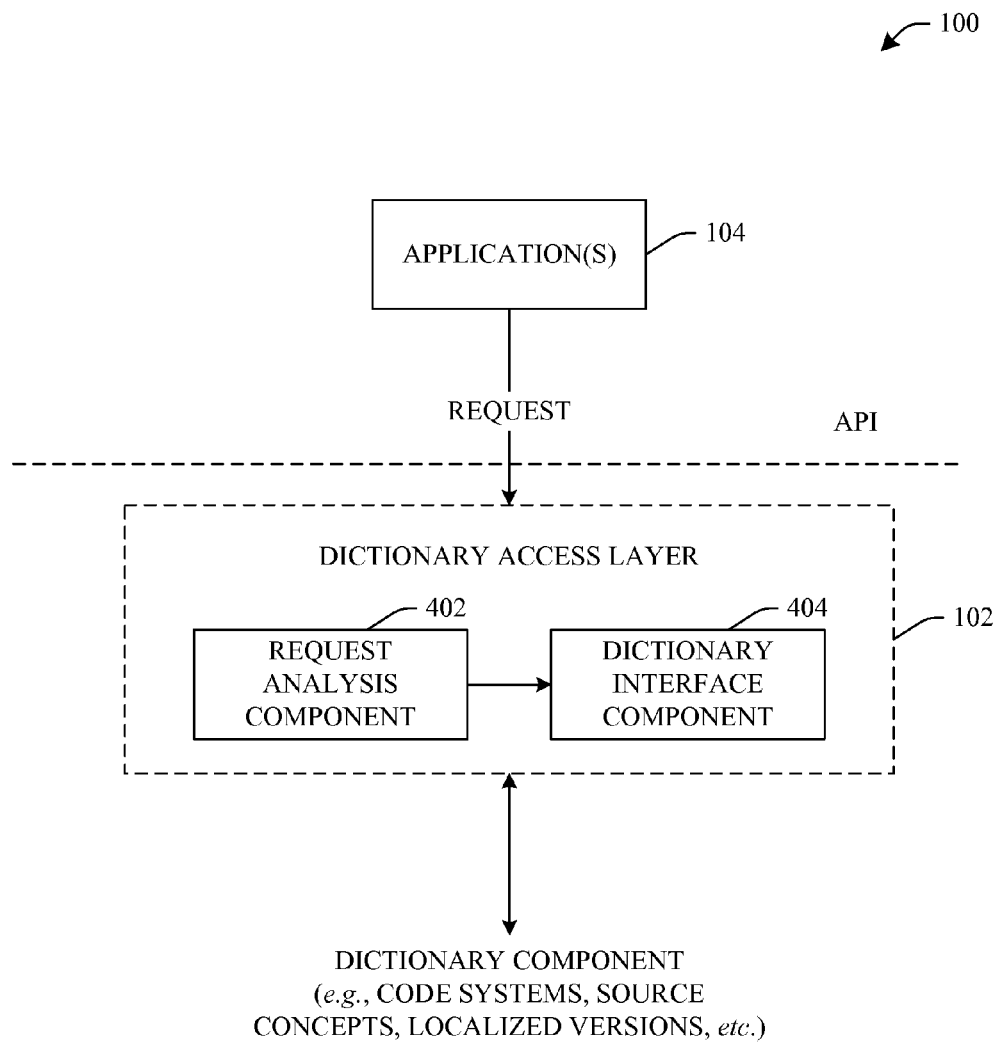
FIG. 4 illustrates an example system that employs a dictionary access layer having request analysis and dictionary interface components in accordance with an aspect of the innovation.

Referring now to FIG. 4, an alternative architectural block diagram of system 100 is shown in accordance with an aspect of the innovation. As illustrated, dictionary access layer 102 can include a request analysis component 402 and a dictionary interface component 404 that together enable a processing a request from an application 104. While specific examples are described herein, it is to be understood that these examples are not intended to limit the innovation in any manner.

In one example, the request analysis component 402 can evaluate the request received from application 104 in order to determine information/processes desired from the dictionary component. Accordingly, the request analysis component 402 provides details of the request to the dictionary interface component 404 whereas the component 404 interacts with the dictionary component to fulfill the request. As described above, the dictionary component, via the interface component 404 can be employed to provide simple definitions (e.g., decipher medical terminology and nomenclature), effect unit transformations, localize health-related information, etc.

Figure 8:
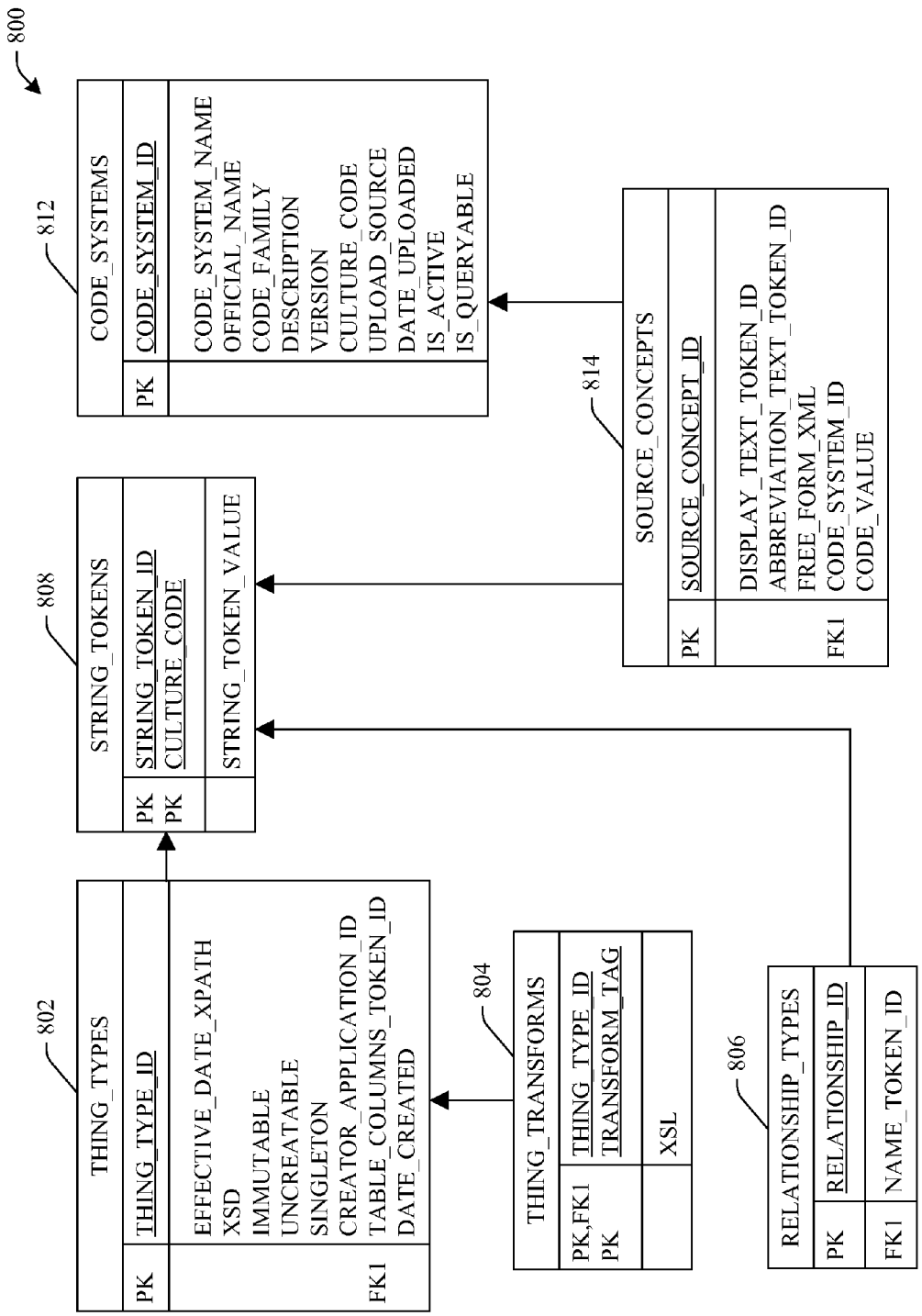
FIG. 8 illustrates an example schema associated with a dictionary in accordance with an aspect of the innovation.

The dictionary interface component 404 enables access to the taxonomy storage and localization (e.g., dictionary component). As disclosed in the identified Related Application as illustrated in FIG. 8 infra, the health taxonomies can each be maintained with its own unique coding system and structural requirements within the dictionary component. These coding systems enable the dictionary interface component 404 to return different variations of the taxonomy localized per the locale of the partner (or application 104) calling the API.

In aspects, the dictionary component can include three collections. A collection of code systems, each represents a separate taxonomy in the dictionary component. A collection of source concepts can be included that represents individual concepts within a taxonomy, wherein the taxonomy can include multiple concepts. Moreover, the dictionary component can include a collection of localized versions of text strings.

Figure 5:
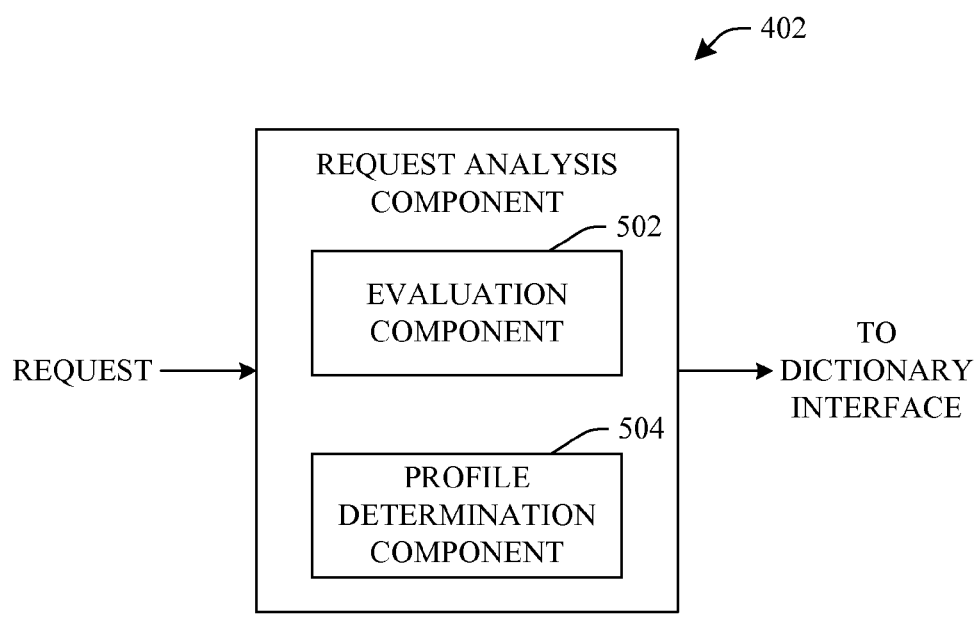
FIG. 5 illustrates an example block diagram of a request analysis component in accordance with an aspect of the innovation.

FIG. 5 illustrates an example request analysis component 402 in accordance with an aspect of the innovation. As shown, the request analysis component 402 can include an evaluation component 502 that can determine specific elements of the request. For instance, the evaluation component 502 can determine if the request is directed to a vocabulary definition, a transformation, a localization, etc. Additionally, specific criteria associated with the request can be established by the evaluation component 502.

The profile determination component 504 can be employed to establish specifics related to a user and/or application profile. For example, where localization is desired, the profile determination component 504 can identify a locale by which to communicate to the dictionary interface component 404. It is to be understood that most any profile parameter (e.g., location, locale, preference, etc.) can be established by the profile determination component 504.

Figure 6:
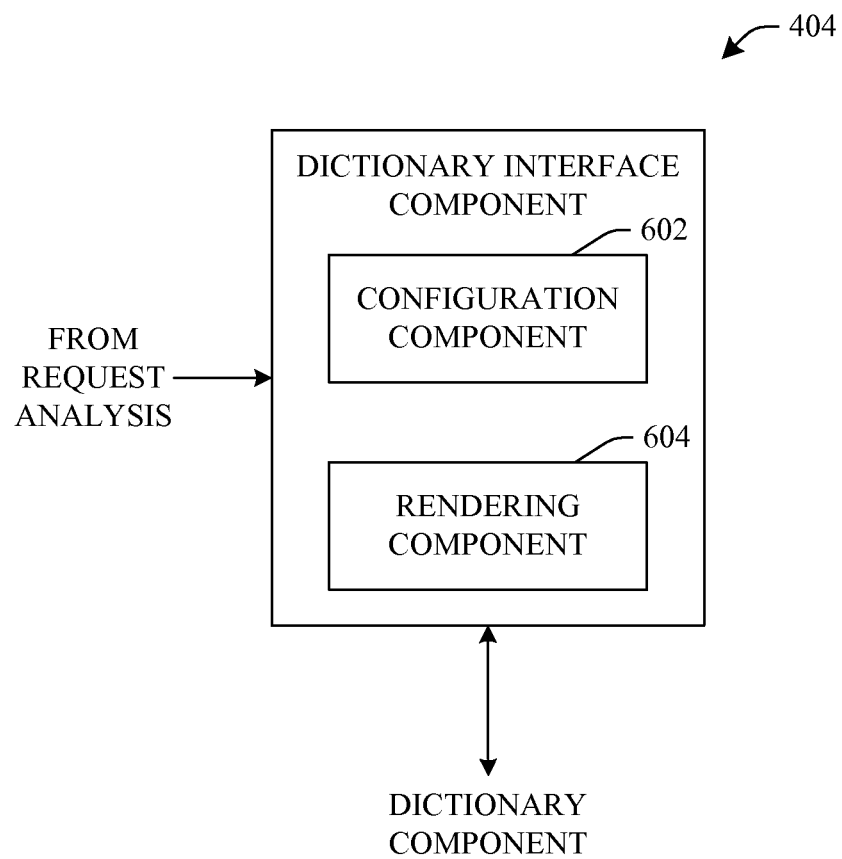
FIG. 6 illustrates an example block diagram of a dictionary interface component in accordance with an aspect of the innovation.

An example dictionary interface component 404 is illustrated in FIG. 6. Generally, the interface component 404 can include a configuration component 602 and a rendering component 604 that facilitate communication between the dictionary component and the application (e.g., 104 of FIG. 1). In other words, the configuration component 602 can receive information from the analysis component 402 and thereafter access data from the dictionary component in furtherance of fulfilling the request. The configuration component 602 can format data, apply transforms or localizations, etc. in accordance with the request.

Thereafter, the rendering component 604 can be employed to communicate the information to the requester (e.g., application 104 of FIG. 1). It is to be understood that the rendering component 604 can deliver data to the requestor in accordance with the requested criteria and/or predefined rule.

Within the dictionary component, each code system or taxonomy can be identified using a multi-part key, for example, a three-part key which includes the name, family and version of the taxonomy. While a three-part key is described, it is to be understood that most any suitable multi-part key can be employed within alternative aspects. The dictionary can also contain additional descriptive information about the taxonomy. In operation, the configuration component 602 employs this information when preparing a response to the request.

Figure 7:
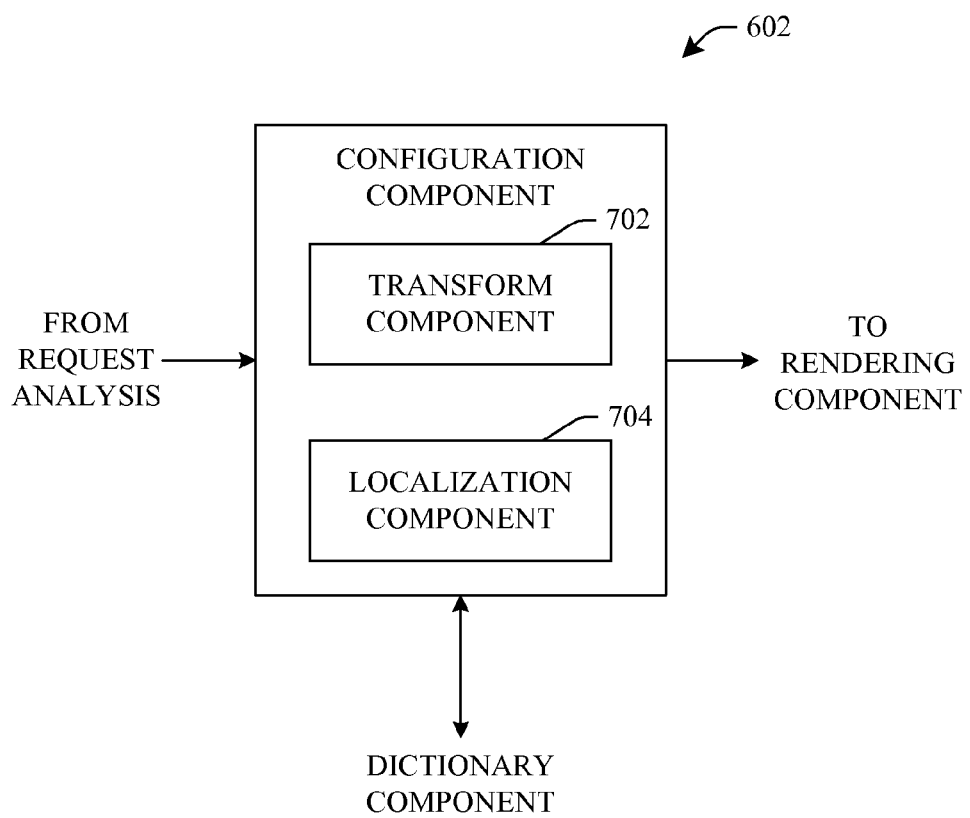
FIG. 7 illustrates an example block diagram of a configuration component in accordance with an aspect of the innovation.

Continuing with the example, each source concept contains a pointer to the code system or taxonomy it belongs to and identifiers for the display text and abbreviation associated with the source concept. The configuration component 602 can use each of these identifiers in conjunction with the supplied locale of the caller to select the appropriate localized form of the display text or abbreviation as a text string from the localized strings collection. As illustrated in FIG. 7, the configuration component 602 can include a transform component 702 and a localization component 704. Essentially, the transform component 702 and localization component 704 employ the information maintained within the taxonomies in order to provide the rendering component 604 with response information to the request.

In addition to this information, each source concept can have associated with it a field (or group of fields) that stores some free form XML (extensible markup language). The XML is used to store structured data that helps use or describe source concepts in its taxonomy. This free form XML assists to associate structure with individual taxonomy elements as per the descriptive/structural requirements of that particular taxonomy. It is reasonable to expect further extensions to both the taxonomies being used in the system and structure used to describe them. Accordingly, these further extensions are to be included within the scope of the innovation and claims appended hereto. In aspects, the rendering component 604 communicates to the API to return to the users the contents of requested taxonomies as lists with localized forms for the display text associated with each source concept in the taxonomy.

The innovation further discloses the use of structures in the dictionary subsystem that can be used by the transform component 702 and localization component 704 to achieve localized transformation of the 'thing' data before presenting it to the caller. Each data item in the system called a 'thing' belongs to a type defined in the system. Associated with each type is a collection of transforms that can be applied on a 'thing' before it is returned by the platform. One good use of these transforms would be to change the representation of the 'thing' for display purposes. The transforms themselves can include text which can have different representations based on the locale of the caller (e.g., application 104 of FIG. 1) fetching the 'thing.' Also the actual applicable transform itself may differ based on the locale of the caller. For example a caller with a locale associated with Arabic may want the contents of the 'thing' rendered right to left or the currency representation in a 'thing' may contain commas or periods depending on the locale.

The system stores, along with a collection of 'thing' transforms per 'thing' type, a collection of localized representations of contents transforms. The transform collection contains, besides a name used to identify the transform, certain basic transforms that are included with every transform before it is applied. The transform can also contain the names of the various vocabularies or taxonomies whose contents are used in the transform.

Additionally, free text used in the transforms that requires localization is itself represented as a special vocabulary in the dictionary and as transform variables in the transform. Upon selecting the appropriate transform to apply on a 'thing', the transform component 702 selects the transform; the various included transforms, and the vocabulary and the transform variables from the transforms store within the dictionary component. Other than free form text, it is to be understood that the transforms can also reference contents of other vocabularies/taxonomies in the system. These taxonomies are therefore also potentially associated with a transform. The representation of the content of the vocabulary before being combined with the transform can be independently based locale.

Similarly, the localization component 704 fetches independently the localized representations for the transform and the included transforms from the localized transforms store within the dictionary component. As well, the localization component 704 fetches the localized representations of the vocabularies and transforms variables from the source concepts store also within the dictionary component. Thereafter, the configuration component 602 combines these representations to create the transform contents to be applied on the 'thing.'

A fallback or default mechanism can be used independently on each part during the fetch of the four parts of this system. If the representation for that part does not exist in the current locale, this fallback mechanism attempts to get a suitable representation in some acceptable locale, for each of the above four parts. The locale in the system can be represented by two parts, the country and the language. In normal operation, the fallback attempts to fetch the representation for the specified locale, followed by the representation for the specified language alone. An example fallback would be to fetch a representation for English and United States locale followed by a representation for the English language.

FIG. 8 illustrates a schema 800 that can be used to define data stored in a dictionary repository in connection with a health integration network as described above. The schema can support storage of records relating to different types, conversions, transforms, data schemas, and the like within the network. In effect, the dictionary repository can provide lookup services for a variety of items to retrieve user-friendly definitions. For example, a THING_TYPES 802 item can exist in the schema to provide a data specification for items related to available data types for 'things' in the network. The THING_TYPES 802 item can require a thing_type_id to uniquely identify respective types within the repository. The item also provides an XML schema definition (XSD) to identify the layout of the data within the type. This can be used to check conformance of data with a specified type to ensure integrity of the data for example. Other values can be provided to identify aspects of the type such as if the type is to be creatable or not, whether the type is immutable, meaning the item is not modifiable after created, and also whether the type is singleton (meaning only one instance exists), and the like. 'Things' in a record repository, such as those conforming to the THINGS item, can utilize this item to store data regarding types relating to those things. The data in the health integration network is further integrated by the schemas in this way. The THING_TYPES 802 item can additionally specify the application which created the data type. It is to be appreciated that once created, data types can be used by disparate application to both request and store data. Examples of thing types definable under this item 802 and part of this schema 800 can be profile (relating the profile of a user), document, fitness_measurement, provider, medication, allergy, lab_result, emergency_contact, data_feed, application specific types (including any types relating to establishments using specific applications such as pharmacy, doctor's office, as well as devices such as those mentioned supra).

A THINGS_TRANSFORM 804 item can additionally exist in the schema 800 to define instructions for transforming given types to another type, format, or architecture. It is to be understood that the thing data of a particular thing type in the system is one being transformed to a representational format. In other words, the thing type is a type in the system that the thing data can belong to and implies the semantics of the data, it is not associated with the representational format. The transforms merely transform a thing from one representational format such as XML to another such as HTML.

For example, a thing_type_id can be provided to identify the type that the thing belongs to. Further, it can be used in conjunction with the supplied transform tag to appropriately identify the transform to be used on the thing. Moreover, an XML stylesheet (XSL) can be stored according to a transform item that can be applied to the data resulting in the appropriate representation of the transformed data. Using this method, many different transform types can be created, including really simple syndication (RSS), any stylized string representations, HTML, and the like. To identify the different types and other items that can be in the dictionary repository, as will be further specified below, the schema 800 can provide a STRING_TOKENS 808 item. This can provide, for example, data such as a string_token_id to uniquely identify the string tokens in the repository that conform to this item specification, as well as the string value. Also, a culture_code can be provided to identify a culture to which the string token can relate; this includes language or dialect and country combinations, for example, such as America/English, UK/English, China/Mandarin, Canada/English, Canada/French, etc. As mentioned, the string can tie back to a thing type to help a user or developer to identify or otherwise display the type.

Additionally, in one aspect, the STRING_TOKENS 808 item can also define data for a RELATIONSHIP_TYPES 806 item, and the associated data can apply labels to relationship types important to a health integration network such as the relationship between two people defined in the PEOPLE item (such as father, mother, spouse, sibling, doctor, personal trainer, etc.). The RELATIONSHIP_TYPES 806 item can have a relationship_id which can be the same as used in previously described schemas, and a name_token_id that can match up with a string_token_id in data defined by the STRING_TOKENS 808 item. It is to be understood that the relationship types described above are an example and are not intended to limit the innovation in any way.

Another example of data that have a definition in the schema 800 is that related to code systems (such as ICD-9 mentioned above). For this data, a CODE_SYSTEMS 812 item can be implemented to conform data related to these systems, providing entries for a code_system_id, for example, to uniquely identify respective code systems available in a health integration network. Additionally, the CODE_SYSTEMS 812 item can also provide a plurality of names representing common names as well as official names. Moreover, a code family can be provided that represents different groupings of codes, as well as a version of the code, culture code (as mentioned above), upload source, and the like. Also, some status identifiers can be provided such as whether or not the code is queryable and active. These can also be state codes conforming to a state schema. Furthermore, a SOURCE_CONCEPTS 814 item can be provided to define different items related to the CODE_SYSTEMS 812 item. For example, a display_text_token_id can be provided that can relate to an item conforming to the STRING_TOKENS 808 item for displaying a user-friendly text string. Additionally an abbreviated version of the string can be provided as well as some free form XML to express the relevant data. Also, the SOURCE_CONCEPTS 814 item can provide the code_system_id to which it relates.

Figure 9:
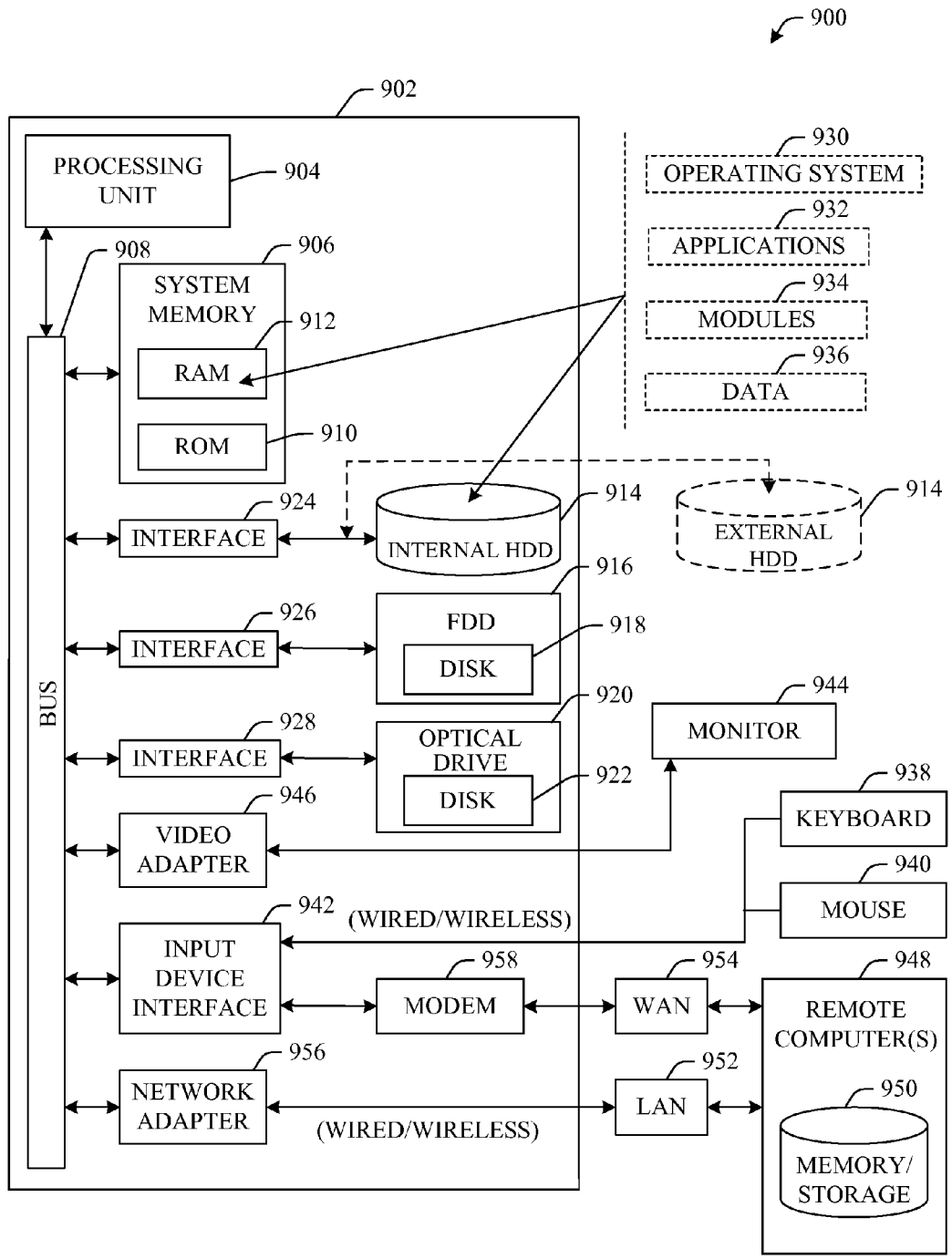
FIG. 9 illustrates a block diagram of a computer operable to execute the disclosed architecture.

Referring now to FIG. 9, there is illustrated a block diagram of a computer operable to execute the disclosed architecture. In order to provide additional context for various aspects of the subject innovation, FIG. 9 and the following discussion are intended to provide a brief, general description of a suitable computing environment 900 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 9, the exemplary environment 900 for implementing various aspects of the innovation includes a computer 902, the computer 902 including a processing unit 904, a system memory 906 and a system bus 908. The system bus 908 couples system components including, but not limited to, the system memory 906 to the processing unit 904. The processing unit 904 can be any of various commercially available processors. Dual microprocessors and other multi-processor architectures may also be employed as the processing unit 904.

The system bus 908 can be any of several types of bus structure that may further interconnect to a memory bus (with or without a memory controller), a peripheral bus, and a local bus using any of a variety of commercially available bus architectures. The system memory 906 includes read-only memory (ROM) 910 and random access memory (RAM) 912. A basic input/output system (BIOS) is stored in a non-volatile memory 910 such as ROM, EPROM, EEPROM, which BIOS contains the basic routines that help to transfer information between elements within the computer 902, such as during start-up. The RAM 912 can also include a high-speed RAM such as static RAM for caching data.

The computer 902 further includes an internal hard disk drive (HDD) 914 (e.g., EIDE, SATA), which internal hard disk drive 914 may also be configured for external use in a suitable chassis (not shown), a magnetic floppy disk drive (FDD) 916, (e.g., to read from or write to a removable diskette 918) and an optical disk drive 920, (e.g., reading a CD-ROM disk 922 or, to read from or write to other high capacity optical media such as the DVD). The hard disk drive 914, magnetic disk drive 916 and optical disk drive 920 can be connected to the system bus 908 by a hard disk drive interface 924, a magnetic disk drive interface 926 and an optical drive interface 928, respectively. The interface 924 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 902, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 912, including an operating system 930, one or more application programs 932, other program modules 934 and program data 936. All or portions of the operating system, applications, modules, and/or data can also be cached in the RAM 912. It is appreciated that the innovation can be implemented with various commercially available operating systems or combinations of operating systems.

A user can enter commands and information into the computer 902 through one or more wired/wireless input devices, e.g., a keyboard 938 and a pointing device, such as a mouse 940. Other input devices (not shown) may include a microphone, an IR remote control, a joystick, a game pad, a stylus pen, touch screen, or the like. These and other input devices are often connected to the processing unit 904 through an input device interface 942 that is coupled to the system bus 908, but can be connected by other interfaces, such as a parallel port, an IEEE 1394 serial port, a game port, a USB port, an IR interface, etc.

A monitor 944 or other type of display device is also connected to the system bus 908 via an interface, such as a video adapter 946. In addition to the monitor 944, a computer typically includes other peripheral output devices (not shown), such as speakers, printers, etc.

The computer 902 may operate in a networked environment using logical connections via wired and/or wireless communications to one or more remote computers, such as a remote computer(s) 948. The remote computer(s) 948 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 950 is illustrated. The logical connections depicted include wired/wireless connectivity to a local area network (LAN) 952 and/or larger networks, e.g., a wide area network (WAN) 954. Such LAN and WAN networking environments are commonplace in offices and companies, and facilitate enterprise-wide computer networks, such as intranets, all of which may connect to a global communications network, e.g., the Internet.

When used in a LAN networking environment, the computer 902 is connected to the local network 952 through a wired and/or wireless communication network interface or adapter 956. The adapter 956 may facilitate wired or wireless communication to the LAN 952, which may also include a wireless access point disposed thereon for communicating with the wireless adapter 956.

When used in a WAN networking environment, the computer 902 can include a modem 958, or is connected to a communications server on the WAN 954, or has other means for establishing communications over the WAN 954, such as by way of the Internet. The modem 958, which can be internal or external and a wired or wireless device, is connected to the system bus 908 via the serial port interface 942. In a networked environment, program modules depicted relative to the computer 902, or portions thereof, can be stored in the remote memory/storage device 950. It will be appreciated that the network connections shown are exemplary and other means of establishing a communications link between the computers can be used.

The computer 902 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 10:
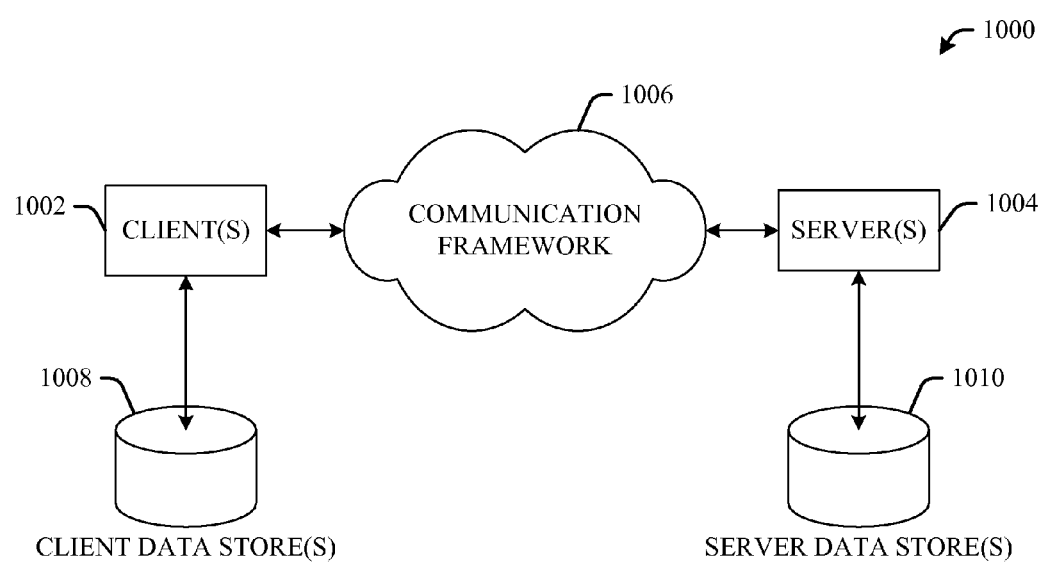
FIG. 10 illustrates a schematic block diagram of an exemplary computing environment in accordance with the subject innovation.

Referring now to FIG. 10, there is illustrated a schematic block diagram of an exemplary computing environment 1000 in accordance with the subject innovation. The system 1000 includes one or more client(s) 1002. The client(s) 1002 can be hardware and/or software (e.g., threads, processes, computing devices). The client(s) 1002 can house cookie(s) and/or associated contextual information by employing the innovation, for example.

The system 1000 also includes one or more server(s) 1004. The server(s) 1004 can also be hardware and/or software (e.g., threads, processes, computing devices). The servers 1004 can house threads to perform transformations by employing the innovation, for example. One possible communication between a client 1002 and a server 1004 can be in the form of a data packet adapted to be transmitted between two or more computer processes. The data packet may include a cookie and/or associated contextual information, for example. The system 1000 includes a communication framework 1006 (e.g., a global communication network such as the Internet) that can be employed to facilitate communications between the client(s) 1002 and the server(s) 1004.

Communications can be facilitated via a wired (including optical fiber) and/or wireless technology. The client(s) 1002 are operatively connected to one or more client data store(s) 1008 that can be employed to store information local to the client(s) 1002 (e.g., cookie(s) and/or associated contextual information). Similarly, the server(s) 1004 are operatively connected to one or more server data store(s) 1010 that can be employed to store information local to the servers 1004.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising at least one processor coupled to at least one machine-readable storage medium storing instructions executable by the at least one processor to implement:
    a dictionary component that includes reference data;
    a dictionary access layer configured to process a health-related data request and render a subset of the reference data based upon the health-related data request; and
    a configuration component configured to transform the subset of the reference data based on a locale associated with the health-related data request, at least in part by selecting and combining localized representations, corresponding to the subset of reference data, to create contents of a transform to be applied to the subset of the reference data to render the subset of the reference data in a localized form, wherein the localized representations include
        information that defines medical acronyms,
        information that defines medical procedures,
        information that defines medical coding vocabulary,
        information that transforms units of measurement, and
        information that formats display characteristics of data, based on the locale associated with the health-related data request.

2. The system of claim 1, wherein the dictionary component includes a plurality of health-related taxonomies.

3. A system, comprising at least one processor coupled to at least one machine-readable storage medium storing instructions executable by the at least one processor to implement:
    a dictionary component that includes reference data;
    a dictionary access layer configured to process a health-related data request and render a subset of the reference data based upon the health-related data request;
    a localization component configured to transform the subset of the reference data based on a locale associated with the health-related data request; and
    a transform component configured to select a transform for a data item to be rendered in the subset of the reference data, from a transforms store associated with the dictionary component;
    wherein the localization component is configured to transform the subset of the reference data based on the locale at least in part by fetching a localized representation corresponding to the transform selected by the transform component from a localized transforms store associated with the dictionary component, wherein the localized representations include
        information that defines medical acronyms,
        information that defines medical procedures,
        information that defines medical coding vocabulary,
        information that transforms units of measurement, and
        information that formats display characteristics of data, based on the locale associated with the health-related data request.

4. The system of claim 1, wherein, to transform the subset of the reference data, the configuration component is configured to translate the subset of the reference data to a local dialect.

5. The system of claim 1, further comprising a request analysis component configured to identify at least one of a name, family or version of taxonomy from the health-related data request, wherein the subset of reference data is associated with the taxonomy.

6. The system of claim 5, further comprising an evaluation component configured to determine a scope of the health-related data request, wherein the scope is to be employed to identify the subset of reference data.

7. The system of claim 6, further comprising a profile determination component configured to establish profile parameters, wherein a subset of the profile parameters are to be employed to identify the locale for which to transform the subset of reference data.

8. The system of claim 5, further comprising a dictionary interface component configured to fetch the subset of reference data from the dictionary component.

9. The system of claim 1, wherein the configuration component is configured to use identifiers of display text associated with a source concept of the dictionary component, in conjunction with the locale, to select a localized form of display text.

10. The system of claim 9, further comprising a rendering component configured to deliver the subset of reference data to an application associated with the health-related data request.

11. The system of claim 10, wherein the rendering component is configured to at least partly employ free form XML (extensible markup language) in rendering the subset of health-related data.

12. A computer-implemented method, comprising:
analyzing, by a computing device, a health-related data request received from an application;
employing, by the computing device, the analysis to identify at least one of a name, family or version of a taxonomy maintained in a dictionary;
retrieving, by the computing device, information from the taxonomy;
creating, by the computing device, contents of a transform to be applied to the information at least in part by selecting and combining localized representations from a transforms store, the localized representations include
information that defines medical acronyms,
information that defines medical procedures,
information that defines medical coding vocabulary,
information that transforms units of measurement, and
information that formats display characteristics of data;
configuring, by the computing device, the information to correspond to a locale at least in part by applying the created transform contents to the information; and
rendering, by the computing device, the configured information to the application.

13. The method of claim 12, further comprising:
partitioning, by the computing device, information of the taxonomy; and
defining, by the computing device, a level of access to a partition of the information.

14. The method of claim 12, further comprising returning, by the computing device, to the application contents of the taxonomy at least partly as a translated form of display text associated with a source concept in the taxonomy.

15. The method of claim of claim 12, further comprising retrieving, by the computing device, profile data, wherein the profile data is employed in the configuring.

16. A computer-readable storage medium storing instructions, the instructions if executed by a computing device causing the computing device to perform operations comprising:
establishing a scope of a health-related data request;
accessing a dictionary for information as a function of the scope;
generating a response to the health-related data request based upon the information;
applying a transform to at least one data item of the information, the transform including a selected combination of localized representations corresponding to the at least one data item;
including the at least one data item to which the transform is applied in the response; and
rendering the response, wherein the localized representations include
information that defines medical acronyms,
information that defines medical procedures,
information that defines medical coding vocabulary,
information that transforms units of measurement, and
information that formats display characteristics of data,
based on a local of the health-related data request.

17. The computer-readable storage medium of claim 16, the rendering the response comprising
associating structure with taxonomy elements of the dictionary,
transforming text associated with the taxonomy by the applying of the transform, and
communicating, via an application programming interface, a content of the taxonomy associated with a source concept in the taxonomy, the content including the transformed text for display.

18. The computer-readable storage medium of claim 16, the operations further comprising accessing a profile in generating the response.

19. The computer-readable storage medium of claim 16, the operations further comprising:
mapping the response to a definition, wherein the response includes the definition; or
transforming the request, wherein the response includes the transformation.

20. The computer-readable storage medium of claim 16, the operations further comprising issuing the response as a default response in the event that a specific response is unavailable.

* * * * *